(12) United States Patent
Bonn

(10) Patent No.: US 8,876,814 B2
(45) Date of Patent: Nov. 4, 2014

(54) FLUID COOLED CHOKE DIELECTRIC AND COAXIAL CABLE DIELECTRIC

(75) Inventor: Kenlyn S. Bonn, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1095 days.

(21) Appl. No.: 12/568,777

(22) Filed: Sep. 29, 2009

(65) Prior Publication Data

US 2011/0077635 A1    Mar. 31, 2011

(51) Int. Cl.
- *A61B 18/18* (2006.01)
- *H01Q 9/16* (2006.01)
- *H01Q 1/27* (2006.01)

(52) U.S. Cl.
CPC ......... *A61B 18/18* (2013.01); *A61B 2018/1892* (2013.01); *A61B 18/1815* (2013.01); *H01Q 9/16* (2013.01); *H01Q 1/27* (2013.01)
USPC ........................................... 606/33; 607/101

(58) Field of Classification Search
USPC ............................... 606/34, 41, 33
See application file for complete search history.

(56) References Cited

U.S. PATENT DOCUMENTS

| | | | |
|---|---|---|---|
| 5,065,819 A | 11/1991 | Kasevich | |
| 5,129,396 A | 7/1992 | Rosen et al. | |
| 5,496,271 A * | 3/1996 | Burton et al. | 607/27 |
| 5,549,639 A | 8/1996 | Ross | |
| 6,134,476 A | 10/2000 | Arndt et al. | |
| 6,175,768 B1 | 1/2001 | Arndt et al. | |
| 6,230,060 B1 * | 5/2001 | Mawhinney | 607/101 |
| 6,330,479 B1 | 12/2001 | Stauffer | |
| 6,699,241 B2 | 3/2004 | Rappaport et al. | |
| 2001/0001314 A1 * | 5/2001 | Davison et al. | 606/41 |
| 2005/0149010 A1 * | 7/2005 | Turovskiy et al. | 606/33 |
| 2007/0203480 A1 | 8/2007 | Mody et al. | |
| 2007/0219551 A1 * | 9/2007 | Honour et al. | 606/41 |
| 2008/0147056 A1 * | 6/2008 | van der Weide et al. | 606/33 |
| 2008/0161890 A1 * | 7/2008 | Lafontaine | 607/105 |

FOREIGN PATENT DOCUMENTS

| | | |
|---|---|---|
| DE | 390937 | 3/1924 |
| DE | 1099658 | 2/1961 |

(Continued)

OTHER PUBLICATIONS

U.S. Appl. No. 08/483,742, filed Jun. 7, 1995.

(Continued)

*Primary Examiner* — Michael Peffley
*Assistant Examiner* — Daniel Fowler

(57) ABSTRACT

The microwave antenna assembly includes a feedline electrically connected to an elongated shaft by a choke electrical connector. The feedline includes an inner conductor, an outer conductor, an elongated shaft and a choke electrical connector. The inner conductor is disposed in coaxial arrangement with the inner conductor and forms a dielectric supply lumen therebetween. The elongated shaft at least partially surrounding the feedline and form a dielectric return lumen therebetween. The choke electrical connector surrounds at least a portion of the feedline and electrically connects the feedline outer conductor to the elongated shaft. A low-loss dielectric fluid is supplied between the inner conductor and the outer conductor of the feedline and forms a dielectric barrier therebetween. The low-loss dielectric fluid also forms a dielectric barrier between the outer conductor of the feedline and the elongated shaft and the choke electrical connector forms a plurality of apertures extending therethrough, the apertures forming at least a portion of the dielectric return lumen.

22 Claims, 4 Drawing Sheets

(56) References Cited

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO 2007/024878 | 3/2007 |

OTHER PUBLICATIONS

U.S. Appl. No. 08/136,098, filed Oct. 14, 1993.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(56) References Cited

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. III, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes To Model Electrical Heating And Non-LInear Thermal Transport In Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College Of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.

(56) References Cited

OTHER PUBLICATIONS

McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (1 Peg) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. On Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.

(56) References Cited

OTHER PUBLICATIONS

European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

FLUID COOLED CHOKE DIELECTRIC AND COAXIAL CABLE DIELECTRIC

BACKGROUND

1. Technical Field

The present disclosure relates generally to microwave surgical devices having a microwave antenna which may be inserted directly into tissue for diagnosis and treatment of diseases. More particularly, the present disclosure is directed to a microwave antenna having a cooled coaxial feed, radiating section and balun choke dielectric and a method of manufacturing the same.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

A typical microwave ablation probe includes a transmission line that provides a microwave energy signal to the microwave antenna. The transmission line is enclosed in an elongated shaft and includes a long, thin inner conductor that extends along the axis of the probe and is surrounded by a dielectric material and is further surrounded by an outer conductor around the dielectric material such that the outer conductor also extends along the axis of the probe.

A cooling system may also be enclosed in the elongated shaft of the microwave ablation probe. For example, cooling fluid may be supplied to the distal end of the microwave ablation probe through one or more cooling supply lumens. After being deposited at the distal end of the elongated shaft the cooling fluid flows proximally through the elongated shaft through a return lumen, typically a chamber between the outer surface of the transmission line and the inner surface of the elongated shaft. In addition to providing cooling for the elongated shaft portion of the microwave ablation probe, the cooling fluid—also at least partially insulates the transmission line from the outer surface of the elongated shaft.

The coaxial construction of the monopole antenna, the dipole microwave antennas and the transmission line that provides a microwave signal thereto, include a dielectric sleeve that provides a dielectric junction between the inner and outer conductors.

Development of structurally stronger invasive probes have resulted in long, narrow, needle-like antenna probes which may be inserted directly into the body tissue to directly access a site of a tumor or other malignancy. Such rigid probes generally have small diameters that aid not only in ease of use but also reduce the resulting trauma to the patient.

Further improvements (i.e., a reduction in diameter, improved temperature management along the shaft and choke, and/or an improvement in strength) may be accomplished by combining the cooling system and the dielectric portions of the transmission line and/or the antenna, as disclosed in the present application.

SUMMARY

The present disclosure provides a surgical microwave antenna assembly and a surgical microwave ablation system. The microwave antenna assembly includes a feedline electrically connected to an elongated shaft by a choke electrical connector. The feedline includes an inner conductor in coaxial arrangement with an outer conductor and forming a dielectric supply lumen therebetween. The elongated shaft at least partially surrounds the feedline and forms a dielectric return lumen therebetween. The choke electrical connector surrounds at least a portion of the feedline and electrically connects the feedline outer conductor to the elongated shaft. A low-loss dielectric fluid is supplied between the inner conductor and the outer conductor of the feedline and forms a dielectric barrier therebetween. The low-loss dielectric fluid also forms a dielectric barrier between the outer conductor of the feedline and the elongated shaft. The choke electrical connector forms a plurality of apertures extending therethrough, the apertures forming at least a portion of the dielectric return lumen.

The dielectric supply lumen and a dielectric return lumen are disposed in fluid communication with each other. The low-loss dielectric fluid, supplied to the dielectric supply lumen and the dielectric return lumen, is configured to absorb thermal energy from the inner conductor and/or the outer conductor.

In one embodiment, the assembly includes an antenna, connected to the distal end of the feedline, configured to radiate microwave energy at a predetermined microwave frequency. The antenna may be at least partially surrounded by a high-dielectric jacket.

In another embodiment, the choke electrical connector forms a Faraday shield to shunt electromagnetic energy radiating proximally from the antenna at the predetermined microwave frequency. The predetermined microwave frequency may be in the range of about 915 MHz to about 2.54 GHz.

The present disclosure further relates to a surgical microwave ablation system, including a microwave signal generator, a low-loss dielectric fluid supply, and a surgical microwave antenna assembly. The surgical microwave antenna assembly includes a feedline, an elongated shaft, a choke electrical connector and a low-loss dielectric fluid. The feedline includes an inner conductor in coaxial arrangement with an outer conductor, the inner conductor and outer conductor forming a dielectric supply lumen therebetween. The elongated shaft at least partially surrounds the feedline, the elongated shaft and the feedline forming a dielectric return lumen therebetween. A choke electrical connector surrounds at least a portion of the feedline and electrically connects the feedline outer conductor to at least a portion of the elongated shaft. A low-loss dielectric fluid is supplied between the inner conductor and the outer conductor of the feedline and forms a dielectric barrier therebetween. The low-loss dielectric fluid also forms a dielectric barrier between the outer conductor of the feedline and the elongated shaft. The low-loss dielectric fluid supply provides the low-loss dielectric cooling fluid to the dielectric supply lumen.

In one embodiment the choke electrical connector of the surgical microwave antenna assembly forms a plurality of apertures extending therethrough, the apertures forming at least a portion of the dielectric return lumen. The low-loss dielectric fluid supply and the dielectric return lumen are in fluid communication through the dielectric supply lumen.

In yet another embodiment, the system further includes an antenna, connected to the distal end of the feedline, configured to radiate microwave energy at a predetermined microwave frequency. The microwave signal generator generates the microwave energy signal and the feedline electrically connects the microwave signal generator to the antenna.

The choke electrical connector of the surgical microwave antenna assembly forms a Faraday shield and is configured to shunt electromagnetic energy radiating proximally from the antenna. The antenna of the surgical microwave antenna assembly is at least partially surrounded by a high-dielectric jacket.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
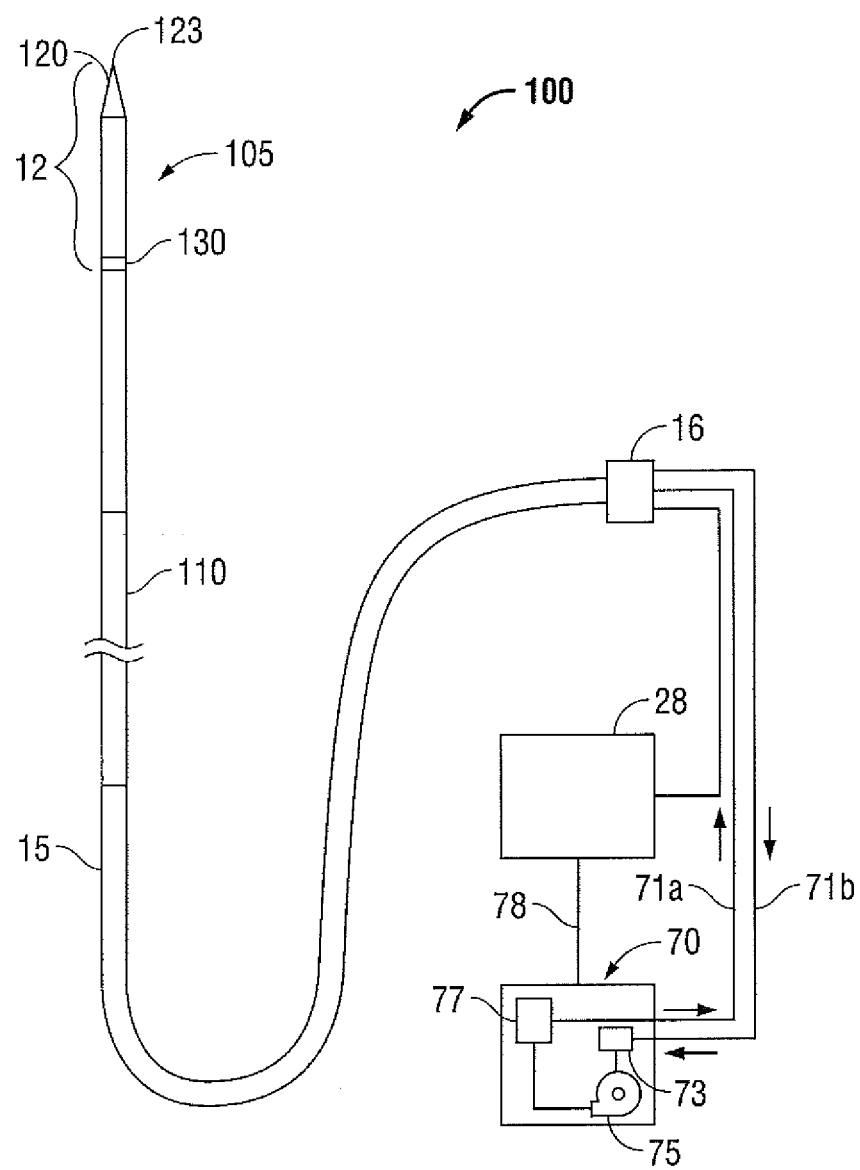
FIG. 1 shows a representative diagram of a variation of a microwave antenna assembly in accordance with an embodiment of the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

FIG. 1 shows an embodiment of a microwave antenna assembly 100 in accordance with the present disclosure. The antenna assembly 100 includes a radiating portion 12 that is connected by elongated shaft 110 via cable 15 to connector 16, which may further connect the assembly 100 to a power generating source 28 (e.g., a microwave or RF electrosurgical generator) and a dielectric cooling fluid supply 70. Assembly 100, as shown, is a monopole microwave antenna assembly, but other antenna assemblies, e.g., dipole or leaky wave antenna assemblies, may also utilize the principles set forth herein. Distal radiating portion 105 of the radiating section 12 includes a tapered end 120 which terminates at a tip 123 to allow for insertion into tissue with minimal resistance. It is to be understood, however, that tapered end 120 may include other shapes, such as without limitation, a tip 123 that is rounded, flat, square, hexagonal, or cylindroconical. Antenna may be positioned using an insertion assistance device such as a catheter, an introducer, an insertion jacket or any other suitable device configured to aid in the positioning of a microwave antenna assembly in tissue.

In the monopole antenna of FIG. 1, the feed point 130 is the portion between the distal end of the feedline (i.e., coaxial cable—not explicitly shown) within the elongated shaft 110 and the distal radiating portion 105. In a dipole antenna, the feed point is the portion between the distal radiating portion and the proximal radiating portion.

Power generating source 28 is configured to generate and provide an electrosurgical signal to the assembly 100. The electrosurgical signal may include a microwave frequency component at 915 MHz, 2.45 GHz or any other suitable frequency.

Dielectric cooling fluid supply 70 is configured to supply a low-loss dielectric cooling solution that does not conduct an electric current at the frequency provided from the power generating source 28. Dielectric cooling fluid may include mineral oil or mineral oil derivatives, soybean oil or a soybean oil derivative, a natural ester-based fluid formulation made from seeds, such as the ester-based fluid sold under the trademark Envirotemp® FR3™ and manufactured and sold by Cooper Power Systems of Waukesha, Wis., a synthetic hydrocarbon fluid such as the synthetic hydrocarbon fluid sold under the trademarks ECO Fluid® and ECO-FR Fluid® manufactured and sold by DSI Ventures, Inc. of Tyler, Tex. Dielectric cooling fluid is selected based on a high degree of biodegradation, environmental compatibility and low toxicity.

The dielectric cooling fluids described in the present disclosure are configured to replace the dielectric materials traditionally provided in microwave antenna assemblies and the feedline that provide the microwave signal to the microwave antenna portion of the microwave antenna assemblies.

In one embodiment, the low-loss dielectric cooling fluid provided to the microwave antenna assembly 100 by the dielectric cooling fluid supply 70 is supplied from the pump 75. Pump 75 draws low-loss dielectric cooling fluid from a supply reservoir (not explicitly shown) and supplies the fluid to the fluid supply 71a. The low-loss dielectric cooling fluid returns from the microwave antenna assembly 100 via the fluid return 71b and is deposited into a return reservoir. The supply reservoir and the return reservoir may or may not circulate fluid therebetween.

In another embodiment, as illustrated in FIG. 1, the dielectric cooling fluid supply 70 is configured to circulate and re-circulate the low-loss dielectric cooling solution through the microwave antenna assembly 100. Fluid supply 71a provides a cooled low-loss dielectric cooling fluid to the connector 16 of the microwave antenna assembly 100. The cooled low-loss dielectric cooling fluid is circulated through the microwave antenna assembly 100 wherein the low-loss dielectric cooling fluid absorbs thermal energy from the microwave antenna assembly. Thermally heated fluid is returned to the dielectric cooling fluid supply 70 through the fluid return 71b. The circulation path of the low-loss dielectric cooling fluid through the distal portion of the microwave antenna assembly 100 is further described hereinbelow and illustrated in FIGS. 2A-4.

Dielectric cooling fluid supply 70 may include a fluid cooling module 73 configured to remove thermal energy from the low-loss dielectric cooling fluid. Fluid cooling module 73 may include active or a passive cooling. Passive cooling may include passing the low-loss dielectric cooling fluid over a thermal energy absorbing material with a high thermal mass or through a thermal energy exchanging module as is known in the art. Active cooling may include a thermoelectric cooling system that uses the Peltier effect to create a heat flux between the junction of two different types of materials. For example, a Peltier cooler or thermoelectric heat pump may transfer heat energy absorbed from the low-loss dielectric cooling fluid by the fluid cooling module 73 to maintain a desirable temperature in the recirculation system. Various devices are know in the art as a Peltier device, a Peltier diode, a Peltier heat pump, a solid state refrigerator, and a thermoelectric cooler (TEC).

Dielectric cooling fluid supply 70 may include a fluid analyzer 77 configured to analyze at least one physical property of the low-loss dielectric cooling fluid. The fluid analyzer 77 may provide an alert, alarm or warning if the analyzed physical property is outside a predetermined range or exceeds a predetermined limit or threshold. For example, fluid analyzer 77 may be configured to sample the impedance of the low-loss dielectric cooling fluid that is returned and/or circulated through the microwave antenna assembly. The analyzer may determine, based on the sampled impedance that a change in impedance of the low-loss dielectric cooling fluid has occurred.

In one embodiment, the fluid analyzer 77 determines if the impedance of the low-loss dielectric cooling fluid is such that a sufficient dielectric barrier in the microwave antenna assembly 100 cannot be maintained. Based on the measured parameter the dielectric cooling fluid supply 70 may take a preventative action such as, for example, alerting the clinician with an audio or visual alarm or alert, providing an alarm to the power generating source 28 that results in the termination of energy delivery and/or providing an alarm to the microwave antenna assembly 100 that may result in the termination of energy delivery to the distal radiating portion 105. Alternatively, the dielectric cooling fluid supply 70 may perform a corrective action such as terminating or diverting the circulation of the low-loss dielectric cooling fluid and introducing a fresh supply of low-loss dielectric cooling fluid from a fluid reservoir into the recirculation path.

In another embodiment, the dielectric cooling fluid supply 70 and power generating source 28 share information via a communication line 78. Information may be shared as one or more analog signals or shared as a digital signal over the communication line 78 by any suitable unidirectional or bidirectional communication protocol. The shared information may include a property of the low-loss, dielectric cooling fluid, a fluid-flow parameter and/or a parameter related to energy delivery.

In one embodiment, the fluid analyzer provides a real-time measurement of the low-loss, dielectric cooling fluid to the power generating source 28 and the power generating source 28 may adjust one or more parameters related to energy delivery. In another embodiment, the power generating source provides a real-time measurement of the impendence or temperature of the distal radiating portion 105 and the dielectric cooling fluid supply 70 may adjust one or more parameters related to fluid flow or fluid supply. For example, a rise in temperature at the distal radiating portion 105 may be corrected by the dielectric cooling fluid supply 70 increasing the flow rate or an impedance change in the fluid or the distal radiating portion 105 may be corrected by adjusting the impedance of the low-loss, dielectric cooling fluid or the output impedance of the power generating source 28.

Figure 2A:
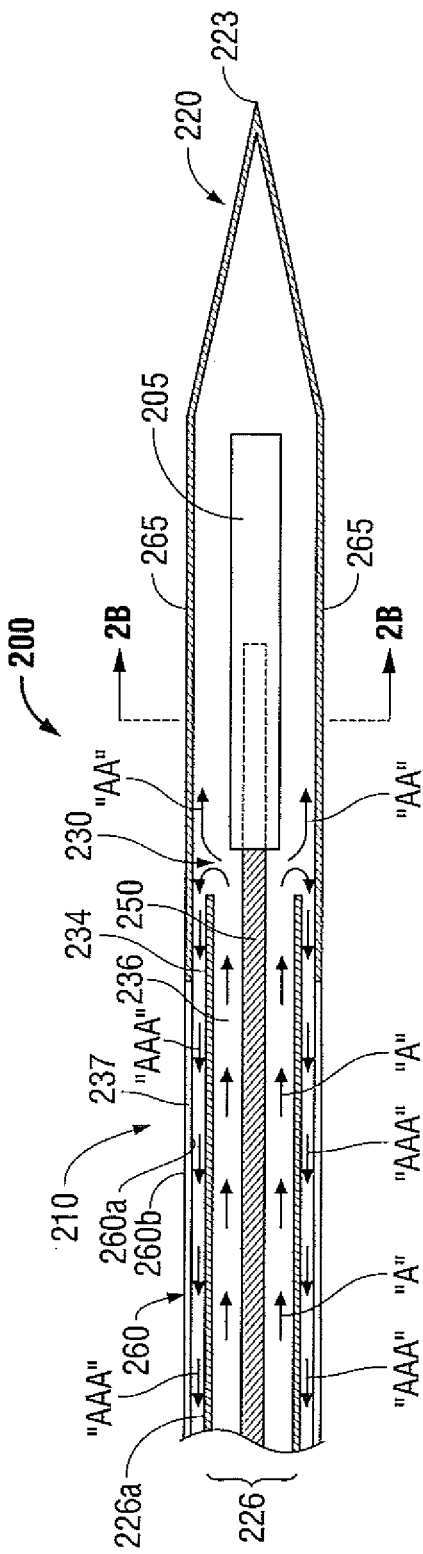
FIG. 2A shows a cross-sectional view of a representative variation of a distal end of microwave antenna assembly of FIG. 1 in accordance with an embodiment of the present disclosure.

FIG. 2A is a cross-sectional view of the distal end of microwave antenna assembly 100 shown as 200. Distal end 200 includes at least a portion of the elongated shaft 210 and the distal radiating section. The elongated shaft includes a feedline 226 and a choke jacket 260. Feedline 226 includes an inner conductor 250 separated from an outer conductor 234 by low-loss dielectric cooling fluid, thereby forming fluid supply lumen 236 therebetween. Inner conductor 250 and outer conductor 234 may be formed from any suitable electrically conductive material. In some embodiments, inner conductor 250 is formed from stainless steel and outer conductor 234 is formed from copper. In one embodiment, the low-loss dielectric cooling fluid forms a dielectric barrier between the inner conductor 250 and the outer conductor 234 such that feedline 226 has an impedance of about 50 ohms.

Choke jacket 260 may be formed from a variety of biocompatible heat resistant, electrically conductive material suitable for penetrating tissue, such as without limitation, stainless steel. Metal jacket of the elongated shaft 110 (see FIG. 1) is proximal the choke jacket 260 and extends the length of the shaft to provide strength and reduce assembly steps. Metal jacket may be formed of stainless steel, a carbon fiber composite or high strength plastic with a conductive surface (i.e., copper, silver, gold or brass) or a silver plated brass. Choke jacket 260 electrically connects to the outer conductor of the feedline 226 and is configured to prevent the proximal propagation of microwave energy. At least a portion of the outer surface 260b of the choke jacket 260 may be coated or covered by a dielectric layer or no-stick layer (not explicitly shown). Coating may include any suitable dielectric material, such as without limitation, ceramic material. In some embodiments, coating may be formed from titanium dioxide and/or zirconium dioxide. Dielectric coating may be applied to choke jacket 260 or may be applied as an additional dielectric coating over the high dielectric jacket 265 of the distal radiating portion 205. Coating may be applied by any suitable process, for example without limitation, plasma spraying or flame spraying. Coating may have a thickness in the range of about 0.005 inches to about 0.015 inches. During an ablation procedure, the dielectric coating may provide improved dielectric matching and/or improved dielectric buffering between the antenna and tissue, which may enable the use of higher power levels, which, in turn, may enable a surgeon to achieve greater ablation rates resulting in increased ablation size, reduced operative times, and/or improved operative outcomes.

With reference to FIGS. 1 and 2A, the fluid supply lumen extends proximally through the length of the elongated shaft 110, the cable 15 and fluidly connects to the fluid supply 71a through connector 16. Pump 75 in dielectric cooling fluid supply 70 pressurizes the fluid supply 71a and the low-loss dielectric cooling fluid flows distally through the fluid supply lumen 236 as indicated by supply flow arrows "A". Low-loss dielectric cooling fluid exits the fluid supply lumen 236 from the distal end of the feedline 226 and is deposited into the feedpoint 230. At least a portion of the low-loss dielectric cooling fluid flows distally into the distal radiating portion 205, as indicated by the distal radiating portion flow arrows "AA", and absorbs thermal energy therefrom.

A fluid return lumen 237 is formed between the outer surface 226a of the feedline 226 and the inner surface 260a of the choke jacket 260. Fluid deposited into the feedpoint 230 and distal radiating portion 205 flows proximally through the fluid return lumen 237 as indicated by return flow arrows "AAA".

With reference to FIGS. 1 and 2, the fluid return lumen 237 extends proximally through the length of the elongated shaft 110, the cable 15 and fluidly connects to the fluid return 71b through connector 16.

With continued reference to FIG. 2A, distal end 200 includes the distal radiating portion 205 at least partially surrounded by a high dielectric jacket 265 that forms a tapered end at the distal portion thereof. Inner conductor 250 is electrically coupled with distal radiating portion 205. High dielectric jacket 265 may be formed from any suitable material, including without limitation polymeric or ceramic materials. In some embodiments, outer jacket 265 is coated with a non-stick coating like a polytetrafluoroethylene (PTFE). a fluorinated ethylene propylene (FEP) or coated with a lubricous spray coat. In another embodiment, the outer jacket 265 is formed of a composite tubing or formed from any suitable non-conductive material.

Figure 2B:
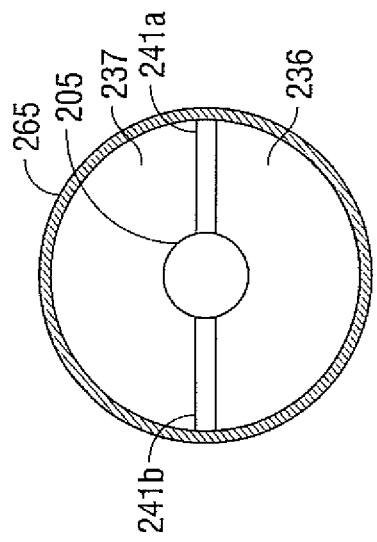
FIG. 2B is a sectional view of the distal radiating section in accordance with another embodiment of the present disclosure.

In another embodiment, the fluid supply lumen 236 and the fluid return lumen 237 extend through the distal radiating portion 205. As illustrated in FIG. 2B, spacers 241a, 241b connect distal radiating portion 205 to the high dielectric jacket 265 thereby dividing the lumen formed therebetween into a portion of the fluid supply lumen 236 and a portion of the fluid return lumen 237. As such, the low-loss dielectric cooling fluid flows distally relative to the distal radiating portion 205 and exits the fluid supply lumen 236 formed between the distal radiating portion 205 and the high dielectric jacket 265. The low-loss dielectric cooling fluid then flows proximally through the fluid return lumen 237 formed between the distal radiating portion 205 and the high dielectric cooling jacket 265.

Figure 3:
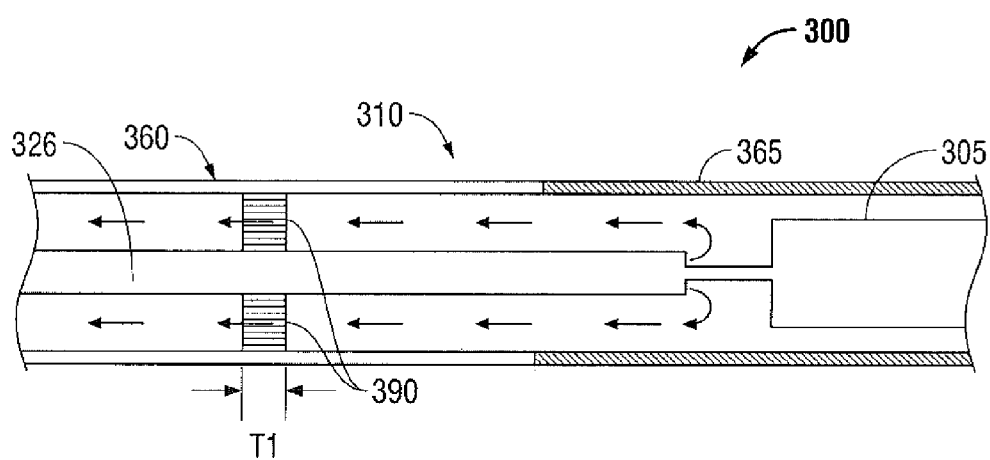
FIG. 3 shows a cross-sectional view of a representative variation of the choked portion of the microwave antenna assembly in accordance with an embodiment of the present disclosure.

Turning now to FIGS. 3, a cross sectional view of the choked portion of the distal end of a microwave antenna assembly 100 of FIG. 1, in accordance with an embodiment of the present disclosure is shown as 300. Choked portion includes a feedline 326 separated from a choke jacket 360 by the choke electrical connector 390. A fluid supply lumen (not explicitly shown) is formed within the feedline 326 as discussed hereinabove and the fluid return lumen 337 is formed between the outer surface of the feedline 326 and the inner surface of the choke jacket 360 and at least a portion of the inner surface of the high dielectric jacket 365.

Choke electrical connector 390 electrically connects the outer conductor (not explicitly shown) of the feedline 326 to the choke jacket 360. Connection may be a weld, solder joint or a press-fit connection or any other suitable connection that provides suitable continuity between the outer conductor of the feedline 326 and the choke jacket 360.

Figure 4A:
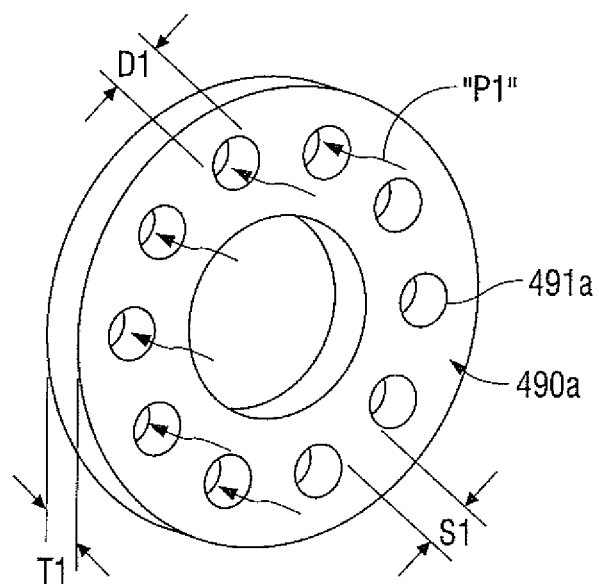
FIG. 4A is an end view of the choke electrical connector from FIG. 3 in accordance with an embodiment of the present disclosure.
Figure 4B:
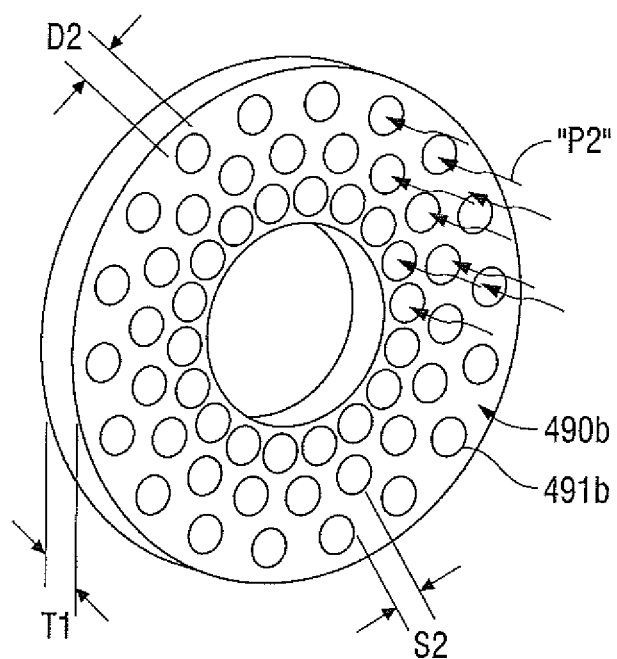
FIG. 4B is an end view of a variation of the choke electrical connector from FIG. 3 in accordance with another embodiment of the present disclosure.

Referring to FIGS. 4A and 4B choke electrical connector 390 also provides a plurality of fluid pathways P1, P2 for fluid to flow distally therethrough the choke electrical connector 390, the fluid pathways P1, P2 forming at least a portion of the fluid return lumen 337. As illustrated in FIGS. 4A and 4B, the fluid pathways P1, P2 are formed through the plurality of apertures 491a, 492b thereby providing a flow path for the low-loss dielectric cooling fluid to flow through the choke electrical connectors 390, 490a, 490b.

With reference to FIGS. 3, 4A and 4B, apertures 491a, 491b of the choke electrical connector 390, 490a, 490b form a Faraday shield configured to shunt any microwave energy that propagates distally from the distal radiating section 305. The effectiveness of the Faraday cage (or shield) is dependent upon the wavelength of the electric or electromagnetic fields produced by the distal radiating section 305 and the geometry of the choke electrical connector 390, 490a, 490b. The thickness T1 of the choke electrical connector 390, the diameter D1, D2 of the apertures 490a, 490b, respectively, and/or the spacing D1, D2 between apertures 490a, 490b, respectively, determine the frequencies that are effectively shunted by the choke electrical connector. For example, the diameter D1, D2 of the apertures 490a, 490b, respectively, must be significantly smaller than the wavelength of the microwave signal radiated by the distal radiating section 305. Similarly, the thickness T1 must be sufficiently thick to effectively shunt the electromagnetic fields generated by the distal radiating section 305.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A surgical microwave antenna assembly, comprising:
    a feedline having a length, the feedline including:
        an inner conductor;
        an outer conductor in a coaxial arrangement with the inner conductor, the inner conductor and outer conductor forming a supply lumen therebetween;
    an elongated shaft, at least partially surrounding the feedline, the elongated shaft and the feedline forming a return lumen therebetween;
    a choke electrical connector including a substantially cylindrical inner surface surrounding the feedline over a portion of the length thereof and configured to electrically connect the outer conductor of the feedline to at least a portion of the elongated shaft; and
    a low-loss dielectric fluid supplied between the inner conductor and the outer conductor of the feedline forming a dielectric barrier therebetween, the low-loss dielectric fluid also forming a dielectric barrier between the outer conductor of the feedline and the elongated shaft,
    wherein the choke electrical connector forms a plurality of apertures extending therethrough, the apertures forming at least a portion of the return lumen.

2. The assembly of claim 1, wherein the supply lumen is disposed in fluid communication with the return lumen.

3. The assembly of claim 2, wherein the low-loss dielectric fluid is configured to absorb thermal energy from one of the inner conductor and the outer conductor.

4. The assembly of claim 1, further comprising: a radiating section connected to the distal end of the feedline and configured to radiate microwave energy at a predetermined microwave frequency.

5. The assembly of claim 4, wherein the radiating section is at least partially surrounded by a high-dielectric jacket.

6. The assembly of claim 4, wherein the choke electrical connector forms a Faraday shield and is configured to shunt electromagnetic energy radiating proximally from the radiating section.

7. The assembly of claim 5, wherein the Faraday shield formed by the choke electrical connector is configured to shunt electromagnetic energy at the predetermined microwave frequency.

8. The assembly of claim 6, wherein the predetermined microwave frequency is about 915 MHz.

9. The assembly of claim 6, wherein the predetermined microwave frequency is about 2.54 GHz.

10. The assembly of claim 1, wherein the plurality of apertures of the choke electrical connector defines a plurality of fluid pathways in a direction along and about a longitudinal axis of the inner conductor.

11. The assembly of claim 1, wherein a spacing of the apertures of the choke electrical connector is selected to determine frequencies that are effectively shunted by the choke electrical connector.

12. A surgical microwave ablation system, comprising:
a microwave signal generator;
a low-loss dielectric fluid supply; and
a surgical microwave antenna assembly, including:
   a feedline having a length, the feedline including:
      an inner conductor;
      an outer conductor in a coaxial arrangement with the inner conductor, the inner conductor and outer conductor forming a supply lumen therebetween;
   an elongated shaft, at least partially surrounding the feedline, the elongated shaft and the feedline forming a return lumen therebetween;
   a choke electrical connector including an annular surface defining an opening therethrough, the annular surface configured to electrically connect the outer conductor of the feedline to at least a portion of the elongated shaft; and
   a low-loss dielectric fluid supplied between the inner conductor and the outer conductor of the feedline and forming a dielectric barrier therebetween, the low-loss dielectric fluid also forming a dielectric barrier between the outer conductor of the feedline and the elongated shaft,
wherein the low-loss dielectric fluid supply provides the low-loss dielectric fluid to the supply lumen, and wherein the choke electrical connector of the surgical microwave antenna assembly forms a plurality of apertures extending therethrough, the apertures forming at least a portion of the return lumen.

13. The system of claim 12, wherein the low-loss dielectric fluid supply and the return lumen are in fluid communication through the supply lumen.

14. The system of claim 13, wherein the low-loss dielectric fluid is configured to absorb thermal energy from one of the inner conductor and the outer conductor.

15. The system of claim 12, wherein the surgical microwave antenna assembly further includes:
   a radiating section connected to the distal end of the feedline and configured to radiate microwave energy at a predetermined microwave frequency,
   wherein the microwave signal generator generates the microwave energy signal and the feedline electrically connects the microwave signal generator to the radiating section.

16. The system of claim 15, wherein the choke electrical connector of the surgical microwave antenna assembly forms a Faraday shield and is configured to shunt electromagnetic energy radiating proximally from the radiating section.

17. The system of claim 16, wherein the radiating section of the surgical microwave antenna assembly is at least partially surrounded by a high-dielectric jacket.

18. The system of claim 16, wherein the Faraday shield formed by the choke electrical connector is configured to shunt electromagnetic energy at the predetermined microwave frequency.

19. The system of claim 18, wherein the predetermined microwave frequency is about 915 MHz.

20. The system of claim 12, wherein the plurality of apertures of the choke electrical connector defines a plurality of fluid pathways in a direction along and about a longitudinal axis of the inner conductor.

21. The system of claim 12, wherein a diameter of the apertures of the choke electrical connector is selected to determine frequencies that are effectively shunted by the choke electrical connector.

22. A surgical microwave antenna assembly, comprising:
a feedline having a length, the feedline including:
   an inner conductor;
   an outer conductor in a coaxial arrangement with the inner conductor, the inner conductor and outer conductor forming a supply lumen therebetween;
an elongated shaft, at least partially surrounding the feedline, the elongated shaft and the feedline forming a return lumen therebetween; and
a choke electrical connector including an inner surface defining an opening therethrough, the inner surface circumferentially disposed in contact with the feedline over a portion of the length thereof and configured to electrically connect the outer conductor of the feedline to at least a portion of the elongated shaft, wherein the choke electrical connector forms a plurality of apertures extending therethrough, the apertures forming at least a portion of the return lumen, wherein a diameter of the apertures is selected to be less than a wavelength of a microwave signal radiated by the surgical microwave antenna assembly during operation thereof.

* * * * *